(12) United States Patent
Nesselhut et al.

(10) Patent No.: US 6,267,994 B1
(45) Date of Patent: Jul. 31, 2001

(54) USE OF EXTRACT OF CIMICIFUGA RACEMOSA

(75) Inventors: Thomas Nesselhut, Goettingen; Cornelia Bodinet; Peter Schneider, both of Salzgitter; Johannes Freudenstein, Goslar, all of (DE)

(73) Assignee: Schaper & Bruemmer GmbH & Co. KG, Salzgitter (DE)

( * ) Notice: Subject to any disclaimer, the term of this patent is extended or adjusted under 35 U.S.C. 154(b) by 0 days.

(21) Appl. No.: 09/134,159

(22) Filed: Aug. 14, 1998

Related U.S. Application Data

(63) Continuation of application No. PCT/DE97/02898, filed on Dec. 12, 1997.

(30) Foreign Application Priority Data

Dec. 14, 1996 (DE) .............................................. 196 52 183

(51) Int. Cl.[7] .................................................. A61K 35/78
(52) U.S. Cl. ............................................................ 424/773
(58) Field of Search ................................ 424/195.1, 773

(56) References Cited

U.S. PATENT DOCUMENTS 5,569,459   10/1996   Shylankevichg .................. 424/195.1

OTHER PUBLICATIONS

Patent abstract of Japan, vol. 15, No. 1 (C–0793), Jan. 7, 1991 & JP 02 255622 A (Tsumura & Co). Oct. 16, 1990.

T. Nesselhut et al., "Untersuchungen Zur Proliferativen Potenz Von Phytopharmaka Mit Ostrogenvahnlicher Wirkung Bei Mammakarzinomzellen,", Archives of Gynecology and Obstetrics, vol. 254, Nos. 1–4, 1993, pp. 817–818, XP002060552.

G. Rauthe; "Wechseljahresbeschwerden bei Mammakarzinompatientinnen," Fortschr. Med. 114, 1996, pp. 26/46–30/48.

*Primary Examiner*—Jean C. Witz
*Assistant Examiner*—Mike Meller
(74) *Attorney, Agent, or Firm*—Foley & Lardner

(57) ABSTRACT

Composition, including pharmaceutical compositions, containing a combination of antiestrogenic compounds. Methods of treatment using extracts of the plant Cimicifuga, alone or in combination with at least one antiestrogenic compound, which avoid or diminish unwanted side-effects and provide increased therapeutic benefit.

17 Claims, 3 Drawing Sheets

USE OF EXTRACT OF CIMICIFUGA RACEMOSA

This application is a con of PCT/DE97/02898 filed Dec. 12, 1997.

BACKGROUND OF THE INVENTION

The invention relates to the use of an extract of *Cimicifuga racemosa* for treating estrogen-dependent tumors.

Extracts of the rhizome of the black cohosh (*Cimicifugae racemosae rhizoma*) exhibit estrogen-like effects. Components which bind specifically to estrogen receptors and are able to lower gonadotropin levels in ovariectomized rats have been found in the extracts. It has therefore proved to be of value to administer these extracts for the purpose of treating climacteric complaints and dysmenorrhea.

The use of estrogen-containing pharmaceuticals for regulating climacteric complaints is out of the question in the case of patients who are at risk of mammary carcinoma since the growth of estrogen-dependent tumors is naturally augmented by administering estrogen. Since the mechanism by which estrogen-analogous substances act is still unclear, a risk of estrogen-dependent tumors has, as a precaution, been regarded as a contraindication in regard to administering these substances.

It has been reported (Nesselhut et al. in TW Gynäkologie (1993) pages 249 to 250) that relatively low concentrations of the plant drugs rhaponticin and Cimicifuga extract augment the proliferation of carcinoma cells in vitro.

It is also known to treat estrogen-dependent tumors with an antiestrogenic active compound. The currently most popular active compound of this type is tamoxifen (Z)-2-[4-(1,2-diphenyl-1-butenyl)phenoxy]-N,N-dimethylethylamine.

For the above mentioned reasons, it was not possible to consider using estrogens or estrogen-analogous substances to regulate the climacteric complaints of the patients who were being treated with an antiestrogen of this nature.

Whether or not the proliferation of mammary tumor cells is inhibited depends on the concentration of the tamoxifen. However, it is not possible to increase the concentration to a range at which proliferation of the tumor cells is reliably prevented, since tamoxifen becomes toxic at these concentrations.

The present invention therefore takes, as its starting point, the problem of achieving tumor therapy even when using relatively low concentrations of anti-estrogen.

SUMMARY OF THE INVENTION

It is therefore an object of the invention to provide compositions which are useful in antitumor therapy, but avoid the toxicity of high doses of known antiestrogenic compounds. According to this object, compounds are provided which comprise an extract of a medicinal plant of the genus Cimicifuga and, preferably, an antiestrogenic compound. In one embodiment, the antiestrogenic compound is tamoxifen. In yet another embodiment, the antiestrogenic compound is genistein.

It is another object of the invention to provide pharmaceutical compositions suitable for use in antitumor therapy that provide a greater degree of tumor inhibition than known antiestrogenic compounds. According to this object, the inventive compositions are admixed with a pharmaceutically acceptable excipient. In a preferred embodiment, the pharmaceutical compositions are provided in a unit dose form, which contains the extract from about 5 mg to about 500 mg of Cimicifuga plant material.

It is yet another object of the invention to provide methods of treating tumors. According to this object, methods are provided that are especially suited for the treatment of estrogen-dependent tumors. Methods are described, comprising administering compositions which comprise Cimicifuga extracts, either alone or in combination with at least one antiestrogenic compound. The combination methods provide greater effectiveness at lower doses of known antiestrogenic compound. In one embodiment, a composition comprising an extract of a medicinal plant of the genus Cimicifuga is administered to a patient in need of treatment in a therapeutically effective amount. In a preferred embodiment, the composition administered further comprises at least one antiestrogenic compound. In another embodiment, the antiestrogenic compound is tamoxifen. In yet another embodiment, the antiestrogenic compound is genistein. In a preferred embodiment, a therapeutically effective amount of the extract includes from about 5 mg to about 500 mg of Cimicifuga plant material daily.

DETAILED DESCRIPTION OF THE INVENTION

Figure 1:
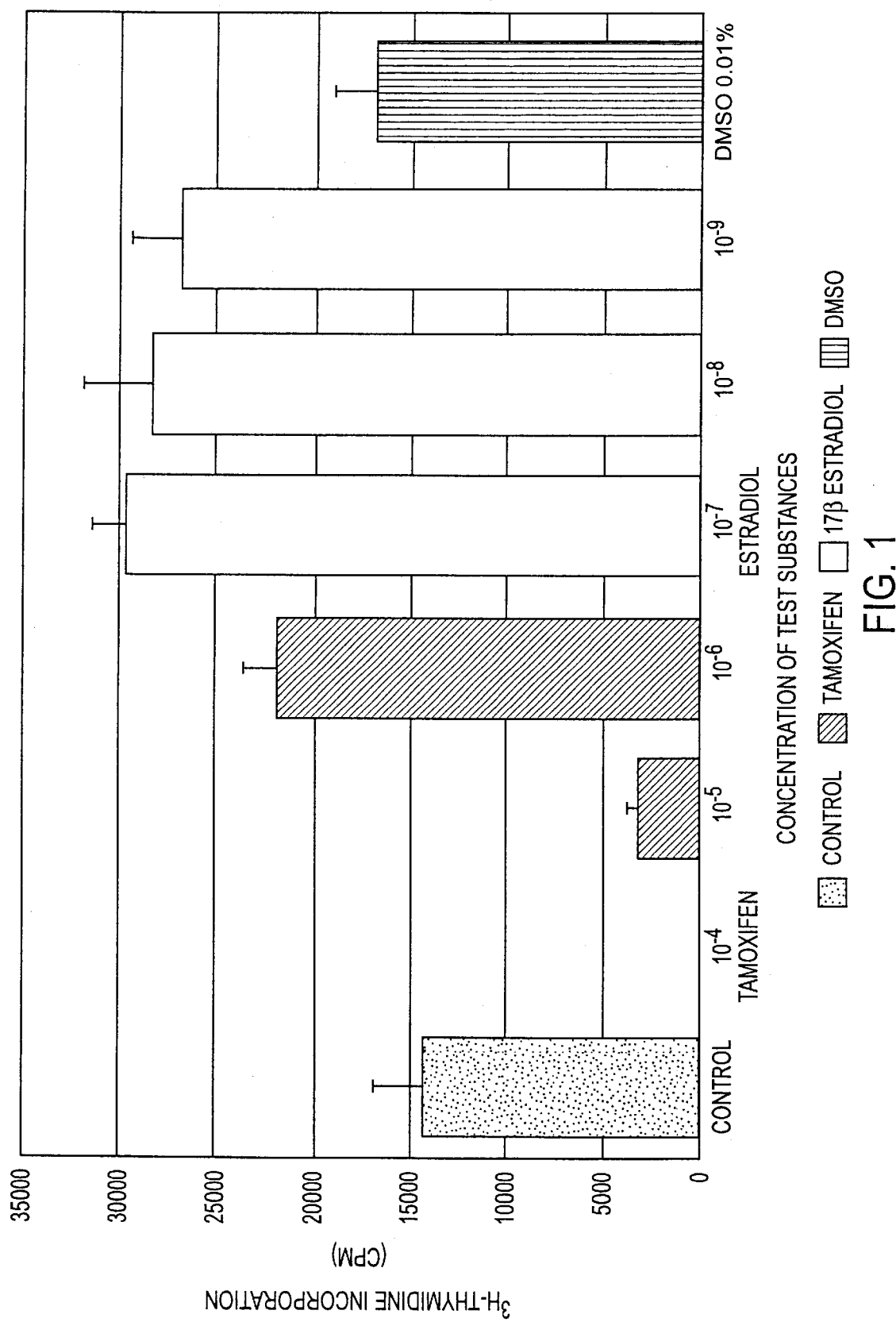
FIG. 1 demonstrates a dose response of MCF 7 mammary carcinoma cells to tamoxifen and estradiol versus control. It can be observed that estradiol stimulates MCF 7 cells at all concentrations, whereas tamoxifen stimulates at low concentrations and inhibits concentrations form 10-4 to 10-5 M.

In a preferred embodiment, the inventors studied the effects of an extract of *Cimicifuga racemosa*, alone or in combination with an antiestrogenic active compound, in a model system which is accepted as predictive of in vivo treatment.

Surprisingly, it was found that the extract of *Cimicifuga racemosa* not only did not augment the proliferation of estrogen-dependent tumor cells, but instead, in combination with an antiestrogenic compound, markedly augments the proliferation-inhibiting effect of this latter compound so that complete inhibition of proliferation can be achieved even without having to enter the range in which the antiestrogenic active compound becomes toxic.

The potentiation of the effect of an antiestrogenic active compound has been investigated in more detail with the aid of the standard active compound tamoxifen. Other experiments indicate that the antiestrogenic effect of genistein is also augmented by an extract of *Cimicifuga racemosa*. Preference is given to dilutions of the extract which are in the range of between about $10^{-3}$ and about $10^{-5}$. Preferred doses are between about 5 mg and about 500 mg of plant material per day.

The compositions of the invention comprise extracts of medicinal plants which contain estrogen-like substances. Preferred plants are from the genus Cimicifuga and the preferred species is *racemosa*. The extracts may be prepared in any suitable manner which maintains or enriches the estrogen-like substances. A preferred method is extraction with a lower alkyl alcohol. A preferred alcohol is isopropanol. The resultant extract maybe maintained as a liquid or converted to another form, such as a dried powder, using conventional means. The form of the extract is not important but it should maintain the activity of the estrogen-like substance. Typical activity may be assayed by reference to the Examples presented below.

Some preferred compositions further comprise at least one antiestrogenic compound. Many such compounds are known to the art. These include tamoxifen and genistein. The relative proportions of extract to antiestrogenic compound will depend on the specific application of the composition. Thus, whereas certain proportions of each compound may be efficacious in treating one type of tumor, entirely different proportions may be beneficial in treating other tumors. Such a determination is well within the purview of the skilled artisan, and may be made with reference to methods such as those in the Examples provided below.

The pharmaceutical compositions of the invention are prepared by admixing a composition, as described above, with a suitable carrier (excipient). Many pharmaceutically acceptable excipients are known in the medical arts. Suitable pharmaceutically suitable excipients, can be found, for example, in REMIGTON'S PHARMACEUTICAL SCIENCES, chapters 83–92, pages 1519–1714 (Mack Publishing Company 1990) (Remington's), which are hereby incorporated by reference. The preferred excipients are those which are inert relative to the active properties of the composition or are enhancing relative to these properties. Thus, these compositions will be suitable for administrations via nearly any medically acceptable route, including oral and parenteral routes.

Some preferred compositions, containing both Cimicifuga extract and at least one other antiestrogenic compound, are formulated such that the amount of the extract enhances the antiestrogenic effect of the antiestrogenic compound and alleviates unwanted side effects, such as estrogen-like stimulation of tumors cells.

The inventive methods comprise administering to a patient in need of treatment of therapeutically effective amount of an inventive composition. Administration may be by any conventional route. The patient may be a human or non-human animal.

The patient generally will be in need of treatment when suffering from a neoplastic or pre-neoplastic disease. A patient will be in need of treatment when the disease is one in which estrogen is involved in the etiology or exacerbation, particularly estrogen-dependent or stimulable tumors. These tumors include, for example, tumors of the female reproductive system and especially mammary tumors.

A therapeutically effective amount typically is an amount that provides a beneficial therapeutic effect. Preferably, this effect is inhibition of tumor cell growth and, most preferably, tumor regression. Of course, therapeutic effectiveness may also be judged according to any other medically acceptable parameters used in the art. Therapeutic effectiveness may be determined with reference to dose response experiments, analogous to those provided in the examples.

Particular dosing regimens will ultimately be determined through clinical trials and will depend upon the judgment of the attending physician. Experiments like those presented below provide a useful benchmark in beginning such evaluation. Further reference will be made to the known clinical profiles of any established antiestrogenic compound used in combination therapy. A preferred dose of extract comprises from about 5 mg to about 500 mg of medicinal plant material per day.

EXAMPLES

The effect, according to the invention, of the Cimicifuga extract on the proliferation of estrogen-dependent carcinoma cells, in particular mammary carcinoma cells, was determined in vitro using a test system of MCF 7 cells.

The MCF 7 cell line is an established in-vitro model for estrogen-dependent tumors which possess both estrogen receptors and aromatase activity. The human breast cancer cell line was derived from a pleural effusion associated with a metastasizing mammary tumor and possesses significant quantities of $17\beta$ receptors (Schwarte, A. (1994) Wirkspektrum ausgewählter Flavonoide auf die humane Brustkrebslinie MCF-7: Eine in vitro Studie [Activity spectrum of selected flavonoids on the human breast cancer cell line MCF 7: An in-vitro study]. Witten-Herdecke, University, Field of Medicine, Dissertation 1994).

The effect of Cimicifuga extract on the proliferation of the MCF 7 cells was determined by measuring the incorporation of radioactively labeled thymidine.

Test Substances $17\beta$-Estradiol (Sigma) and tamoxifen citrate (Sigma) were dissolved in 1M DMSO (dimethyl sulfoxide) and subjected to further appropriate dilution in cell culture medium in a 1:10 dilution series. Cimicifuga extract was diluted directly with cell culture medium in a 1:10 dilution series.

Preparation of the *Cimicifuga racemosa* Extract

After having been checked for identity, purity and content, 30 kg of the comminuted medicinal plant material *Cimicifuga racemosa* rhizoma were macerated for 10 days with 50l of 40% (v/v) isopropyl alcohol. The extract was drained off and the plant material was squeezed out. The combined fractions were made up with 40% (v/v) isopropyl alcohol to a final volume of 35l.

MCF 7 Proliferation Assay

MCF 7 cells were obtained from the ATCC (HTB 22) and cultured in Eagle's MEM (Eagle's minimal essential medium) containing nonessential amino acids, 1 mM sodium pyruvate, 10 $\mu$g/ml insulin and 10% FCS (fetal calf serum).

Before being used in the test, the MCF 7 cells were maintained for at least one passage in Eagle's MEM without phenol red but containing nonessential amino acids, 1 mM sodium pyruvate, 10 $\mu$g/ml insulin and 5% FCS (fetal calf serum). In order to obtain estrogen-free growth conditions in the test, the insulin was removed from the cell culture medium, and the FCS was replaced with 5% charcoal-stripped FCS (CSF), in the case of the test mixture.

200 $\mu$l of a cell suspension which was adjusted to $5\times10^4$ c/ml were pipetted into each well of Nunc 96-well microtiter plates, and the plates were incubated at 37° C. and 5% $CO_2$ for 24 h in an incubator. After that, the supernatants were carefully taken off and 150 $\mu$l of fresh cell culture medium were pipetted into each well.

The test substances were dissolved and the solutions were diluted in cell culture medium; 4 parallel samples of each dilution were then pipetted into the plates at a rate of 50 $\mu$l/well. Cell culture medium and the corresponding solvent dilutions were in each case incubated concomitantly as controls.

After the plates had been incubated at 37° C. and 5% $CO_2$ for 2–3 days, the cells were pulsed for 8 h with (6-$^3$H) thymidine (Amersham, spec. activity 2 Ci/mmol), 25 μl of which were added/well. After that, the cells were harvested on glass fiber filters using standard methods (Cell Harvester, Inotech) and counted in a liquid scintillation counter (Wallac). The results were expressed as cpm=counts per minute.

Preparation of the Charcoal-stripped FCS (CSF)

One dextran-coated charcoal tablet (Steranti Separe) was dissolved in 10 ml of FCS. After that, the serum was inactivated at 56° C. for 2×45 min in a water bath and then centrifuged at 3000 rpm for 10 min. The supernatant was taken off and filtered through a filter having a pore size of 0.2 μm.

Toxicity Assay

A fluorescence assay using HeLa cells in suspension was carried out in order to determine the toxicity of the individual test substances.

HeLa cells were adjusted to a cell density of 2.5×10$^5$ c/ml of medium (Eagle's MEM+5% FCS), and 100 μl of the suspension were pipetted into Nunc 96-well microtiter plates. After the plates had been incubated at 37° C. and 5% $CO_2$ for 24 h, the test substances were diluted in medium in a 1:10 dilution series and 4 parallel samples of each dilution were pipetted into the plates at a rate of 100 μl per well. The mixtures were incubated at 37° C. and 5% $CO_2$ for 48 h. After that, the microtiter plates were centrifuged at 800 rpm and the supernatants were carefully removed. 200 μl of a solution consisting of 0.1 mg/ml 4-methylumbelliferyl heptanoate in PBS were pipetted into each well. After 60 min, the fluorescence units per well were determined in a microtiter plate fluorimeter (Fluoroscan II).

Results

The sensitivity of the test system was first of all checked when the investigations were started. 17 β estradiol, at $10^{-7}$, $10^{-8}$ and $10^{-9}$ molar concentrations, was tested as the positive control.

At all three concentrations tested, 17 β estradiol induced an 80–100% increase in the proliferation of MCF 7 cells as compared with the untreated control, as can be seen from FIG. 1.

A solvent control was carried out in parallel in each test assay. At the maximum concentration at which it was used in the test, DMSO did not bring about any significant increase in, or inhibition of; proliferation as compared with the untreated control.

The effect of the nonsteroidal antiestrogen tamoxifen on the test system was examined in another assay.

At $10^{-4}$ and $10^{-5}$ molar concentrations, tamoxifen caused 100% and 77%, respectively, inhibition of proliferation; by contrast, at concentrations of $10^{-6}$, tamoxifen increased the incorporation rates by 52% as compared with the untreated control.

The antiproliferative effect of tamoxifen was also evident when it was used in the presence of a constant concentration of estradiol. The estrogen-induced increase in proliferation was inhibited by tamoxifen in a concentration-dependent manner.

The results of these preliminary experiments made it clear that the MCF 7 test system is suitable for detecting both estrogenic and antiestrogenic effects of test substances.

In order to monitor this, a positive control for an estrogenic effect, consisting of 17 β estradiol at a $10^{-7}$ or $10^{-8}$ molar concentration, and a positive control for an antiestrogenic effect, consisting of tamoxifen at a $10^{-5}$ molar concentration, were in each case included in the following experimental series in addition to medium controls and solvent controls (negative controls).

Before the Cimicifuga extract was used in the MCF 7 system, its toxicity was first of all checked in a toxicity assay using HeLa cells.

Figure 2:
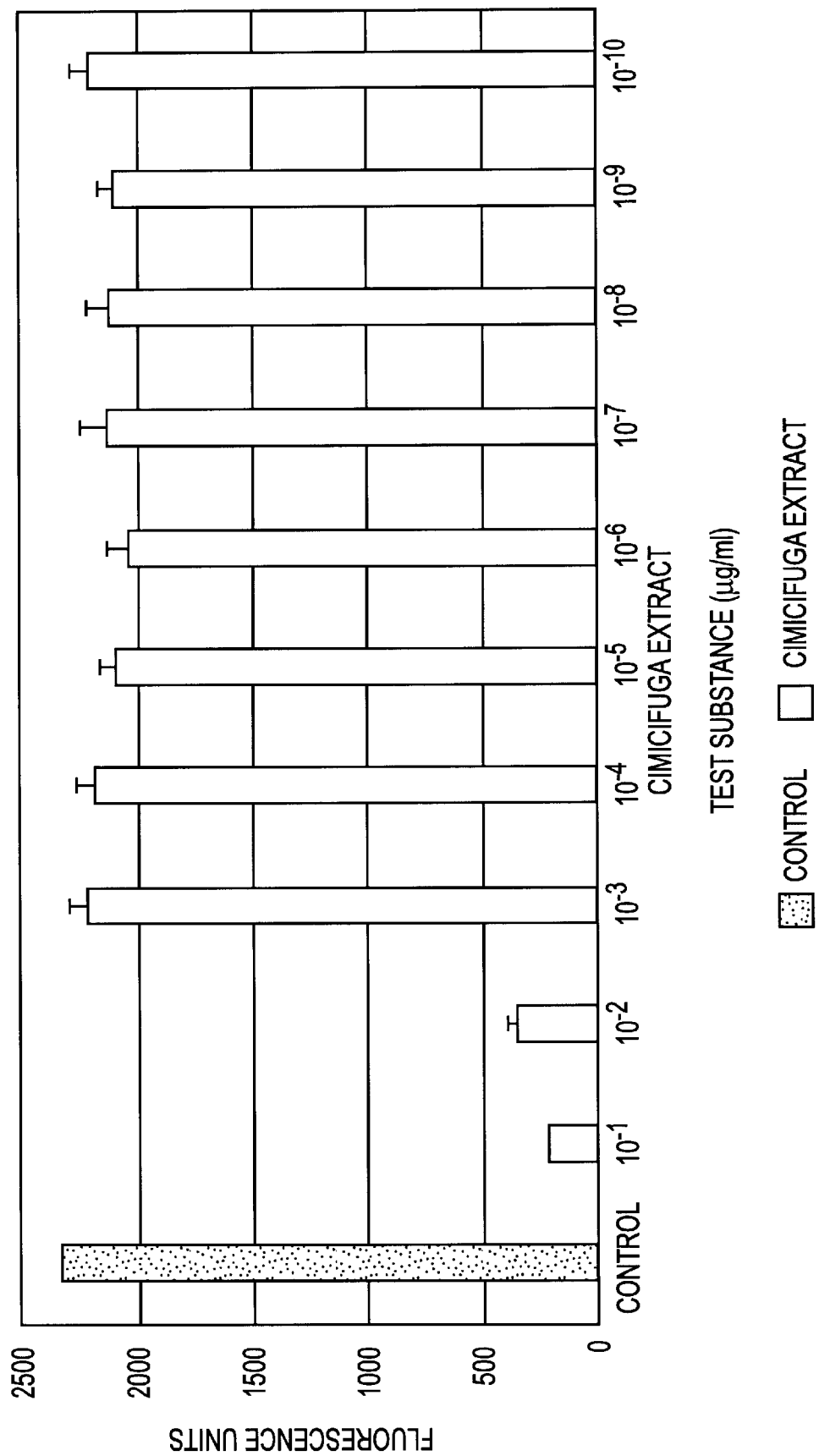
FIG. 2 provides a dose response of MCF 7 cells to a representative Cimicifuga extract. Notably, the inventive extracts do not exert cytotoxic effects in dilutions above $10^{-2}$.

Down to a dilution of $10^{-2}$, the extract displayed toxic effects on this cell line. From a dilution of $10^{-3}$ onwards, it was not possible to observe any differences between the medium control and the test assay (FIG. 2). In order to be able to exclude nonspecific cytotoxic effects, this dilution was therefore used as the maximum concentration for the test series using MCF 7 cells.

Figure 3:
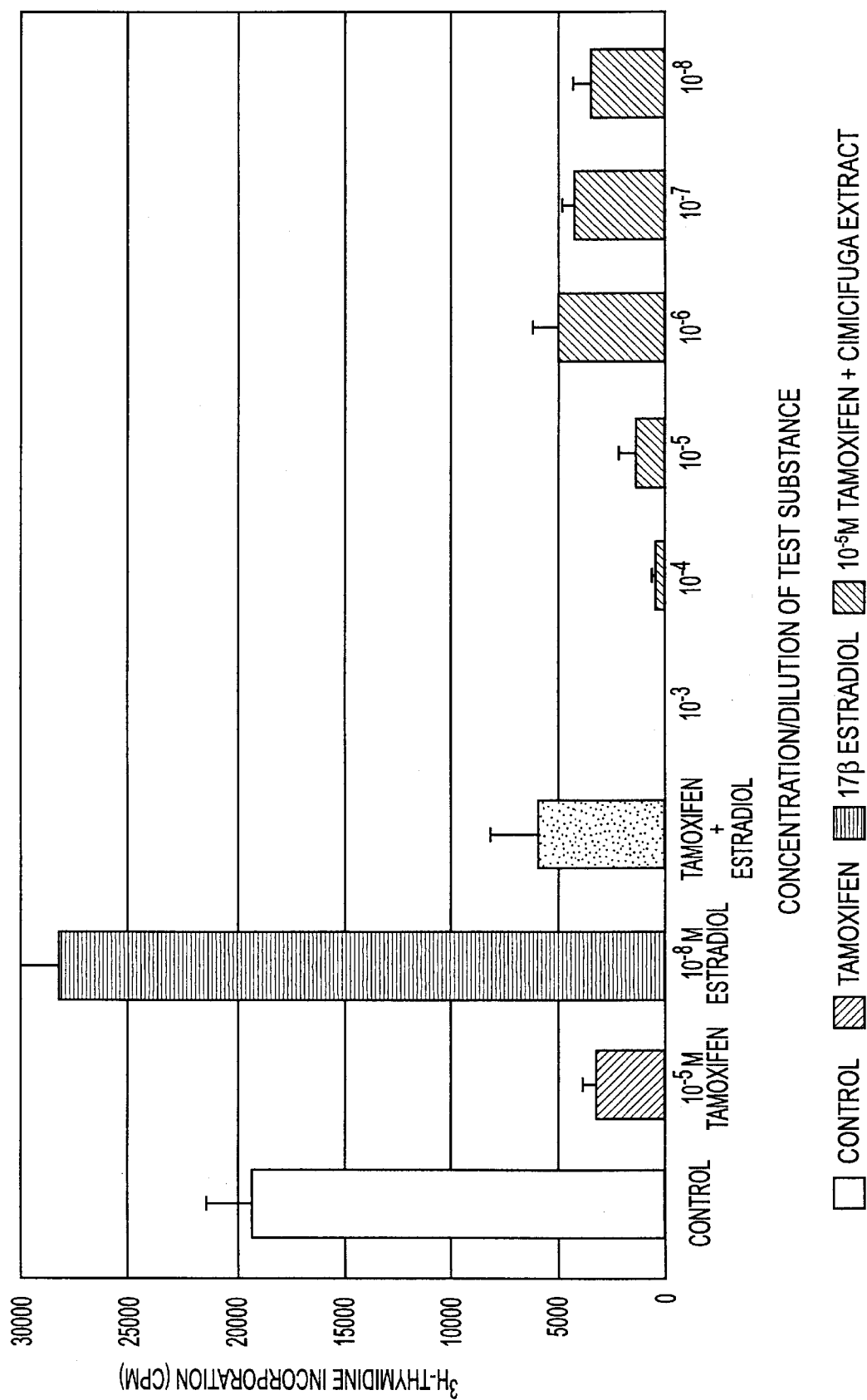
FIG. 3 provides a dose response of MCF 7 cells to a combination of tamoxifen and Cimicifuga extract. It can be observed that the inventive extract augments the induced inhibition of cell proliferation in dilutions ranging from about $10^{-3}$ to $10^{-5}$.

FIG. 3 compares the proliferation which is observed with the control system, that which is observed with a $10^{-5}$ molar tamoxifen solution, that which is observed with a $10^{-8}$ molar estradiol solution and that which is observed with a combination of tamoxifen and estradiol, in order to verify as well the inhibition of estrogen-induced proliferations which is brought about by tamoxifen.

FIG. 3 also shows the inhibition of proliferation which is brought about by combinations of $10^{-5}$ molar tamoxifen with *Cimicifuga racemosa* extract used at various 1:10 dilutions of between $10^{-3}$ and $10^{-8}$. It is found that the proliferation-inhibiting effect of tamoxifen is markedly augmented at the dilutions of $10^{-3}$ to $10^{-5}$, with proliferation being completely suppressed at the dilution of $10^{-3}$ and almost completely suppressed at the dilution of $10^{-4}$.

The combination of tamoxifen with the Cimicifuga extract at a dilution of $10^{-3}$ or $10^{-4}$ can therefore be used to achieve an almost complete inhibition of the pro-liferation of the tumor cells without resort to higher tamoxifen concentrations.

The foregoing examples and description of the invention are provided solely for illustrative purposes and are not intended to be limiting. One skilled in the art will readily recognize additional embodiments within the scope of the invention.

German Patent Application No. 19652183.1 filed Dec. 14, 1996 is hereby incorporated by reference in its entirety.

What is claimed is:

1. A pharmaceutical composition for treatment of cancer, comprising an effective amount of extract of Cimicifuga and an effective amount of at least one antiestrogenic compound.

2. A composition according to claim 1 wherein said extract is alcohol-based.

3. A composition according to claim 2, wherein said alcohol is isopropyl alcohol.

4. A composition according to claim 1, wherein said compound is tamoxifen.

5. A composition according to claim 1, wherein said compound is genistein.

6. A pharmaceutical composition for treatment of cancer, comprising an effective amount of extract of Cimicifuga, an effective amount of at least one antiestrogenic compound and a pharmaceutically acceptable excipient.

7. A pharmaceutical composition according to claim 6, wherein said extract is alcohol-based.

8. A pharmaceutical composition according to claim 7, wherein said alcohol is isopropyl alcohol.

9. A pharmaceutical composition according to claim 6, wherein said compound is tamoxifen.

10. A pharmaceutical composition according to claim 6, wherein said compound is genistein.

11. A pharmaceutical composition according to claim 6, which is formulated as a unit dose and contains from about 5 mg to about 500 mg of plant material.

12. A method of treatment of cancer, comprising administering to a cancer patient a therapeutically effective amount of an extract of Cimicifuga and an antiestrogenic compound.

13. A method of treatment according to claim 12, wherein said wherein said extract is alcohol-based.

14. A method of treatment according to claim 13, wherein said alcohol is isopropyl alcohol.

15. A method of treatment according to claim 12, wherein said compound is tamoxifen.

16. A method of treatment according to claim 12, wherein said compound is genistein.

17. A method of treatment according to claim 12 wherein said administration results in the daily delivery of about 5 mg to about 500 mg of Cimicifuga plant material to said patient.

* * * * *